United States Patent
Lee et al.

(10) Patent No.: US 10,137,262 B2
(45) Date of Patent: Nov. 27, 2018

(54) SYNCHRONIZING MECHANICAL IN-EXSUFFLATION AND DIAPHRAGMATIC PACING

(71) Applicant: KONINKLIJKE PHILIPS N.V., Eindhoven (NL)

(72) Inventors: Seunghyun Lee, Murrysville, PA (US); Richard Grace, Monroeville, PA (US); Michael Howard Kissel, Swissvale, PA (US); Mark Christopher McDermott, Pittsburgh, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 613 days.

(21) Appl. No.: 14/422,013

(22) PCT Filed: Aug. 13, 2013

(86) PCT No.: PCT/IB2013/056609
§ 371 (c)(1),
(2) Date: Feb. 17, 2015

(87) PCT Pub. No.: WO2014/030099
PCT Pub. Date: Feb. 27, 2014

(65) Prior Publication Data
US 2015/0231348 A1 Aug. 20, 2015

Related U.S. Application Data (60) Provisional application No. 61/684,872, filed on Aug. 20, 2012.

(51) Int. Cl.
*A61M 16/00* (2006.01)
*A61N 1/36* (2006.01)

(52) U.S. Cl.
CPC ....... *A61M 16/0003* (2014.02); *A61N 1/3601* (2013.01); *A61M 2205/054* (2013.01); *A61M 2230/005* (2013.01); *A61M 2230/40* (2013.01)

(58) Field of Classification Search
CPC .......... A61M 16/0003; A61M 16/0009; A61M 16/00; A61M 16/0066; A61M 16/0051;
(Continued)

(56) References Cited

U.S. PATENT DOCUMENTS

| 6,360,740 B1* | 3/2002 | Ward | A61N 1/3601 128/200.24 |
| 2005/0021102 A1 | 1/2005 | Ignagni | |
| 2005/0039749 A1* | 2/2005 | Emerson | A61M 16/00 128/204.23 |

FOREIGN PATENT DOCUMENTS

| CA | 20088730 A1 | 8/1993 |
| EP | 0993841 A1 | 4/2000 |

(Continued)

OTHER PUBLICATIONS

Chatwin, M., "Mechanical Aids for Secretion Clearance", Academic and Clinical Department of Sleep and Breathing, Royal Brompton Hospital, London, UK, International Journal of Respiratory Care | Autumn/Winter 2009, pp. 50-53.

*Primary Examiner* — Gregory Anderson
*Assistant Examiner* — Margaret Luarca
(74) *Attorney, Agent, or Firm* — Michael W. Haas (57) ABSTRACT

Systems and methods for synchronizing machine-induced inexsufflation with diaphragmatic pacing of a subject, e.g. through a diaphragm pacer, use the detected onset of an inhalation and/or exhalation of a subject. The detection is based on output signals generated by one or more sensors.

18 Claims, 4 Drawing Sheets

(58) Field of Classification Search
CPC .......... A61M 16/0069; A61M 16/0883; A61M 16/161
See application file for complete search history.

(56) References Cited

FOREIGN PATENT DOCUMENTS

| | | |
|---|---|---|
| EP | 1663361 B1 | 1/2012 |
| WO | WO2007054829 A2 | 5/2007 |
| WO | WO2010058308 A2 | 5/2010 |
| WO | WO2012045735 A1 | 4/2011 |
| WO | WO2012042255 A1 | 4/2012 |
| WO | WO2012080892 A1 | 6/2012 |

* cited by examiner

SYNCHRONIZING MECHANICAL IN-EXSUFFLATION AND DIAPHRAGMATIC PACING

CROSS-REFERENCE TO RELATED APPLICATIONS

This patent application claims the priority benefit under 35 U.S.C. § 371 of international patent application no. PCT/IB2013/056609, filed Aug. 13, 2013, which claims the priority benefit under 35 U.S.C. § 119(e) of U.S. Provisional Application No. 61/684,872 filed on Aug. 20, 2012, the contents of which are herein incorporated by reference.

BACKGROUND OF THE INVENTION

1. Field of the Invention

The present disclosure pertains to systems and methods for inexsufflating a subject using machine-induced inexsufflation, and, in particular, inexsufflating a subject during the use of a diaphragm pacing device.

2. Description of the Related Art

Various systems for increasing patient cough flow through inexsufflation are known. Conventional inexsufflation is generally accomplished using a single inexsufflation event including a single exhalation of the subject. A respiratory circuit and/or the subject may positively pressurize the airway of the subject, and then the respiratory circuit and/or the subject may suddenly reverse the pressure and expel all (or substantially all) of this gas. Secretions built up in the airway of the subject over time may thus be expelled with the gas. Control of the operation of conventional systems used for inexsufflation may include setting an inspiratory pressure and/or one or more time parameters related to the duration of inhalation and/or exhalation. It is known that conventional systems used for inexsufflation may operate in conjunction with a respiratory therapy device that provides mechanical ventilation of a subject, such as a ventilator.

It is known that the breathing pattern of a subject may be characterized by one or more of a breathing rate (a.k.a. respiratory rate), inhalation periods, exhalation periods, pause periods, and/or other characteristics, parameters, and/or periods. The efficacy of machine-induced or mechanical inexsufflation of a subject may be improved by aligning the timing of an inexsufflation relative to the breathing pattern of the subject.

It is known that some patients may benefit from a diaphragm pacing device to assist and/or control their breathing pattern. Under certain (medical) conditions and/or circumstances, a diaphragm pacing device may be used in place of and/or preferred over a ventilator.

SUMMARY OF THE INVENTION

Accordingly, it is an object of one or more embodiments of the present invention to provide a system for synchronizing machine-induced inexsufflation with diaphragmatic pacing of a subject. The system comprises a pressure generator, one or more sensors, one or more processors, a configuration module, a detection module, a target module and a control module. The pressure generator is configured to generate a pressurized flow of breathable gas for delivery to an airway of the subject. The one or more sensors are configured to generate one or more output signals conveying information related to one or both of one or more gas parameters of a flow of breathable gas being breathed by the subject and/or one or more respiratory parameters of the subject. The one or more processors are configured to execute computer program modules. The configuration module is configured to obtain one or more configurable operational settings of diaphragmatic pacing of the subject. The detection module is configured to detect onsets of inhalations of the subject such that, for a first respiratory cycle, the detection module detects an onset of a first inhalation of the subject based on one or more output signals. The first inhalation is included in a first respiratory cycle. The target module is configured to determine a target parameter for machine-induced inexsufflation during respiratory cycles such that, responsive to detection of the onset of the first inhalation, the target module determines the target parameter for machine-induced inexsufflation during a second respiratory cycle in synchrony with diaphragmatic pacing of the subject. The second respiratory cycle is subsequent to the first respiratory cycle. The target parameter is an onset of inhalation during the second respiratory cycle or an onset of exhalation during the second respiratory cycle. The control module is configured to control the pressure generator to inexsufflate the subject such that during the second respiratory cycle the control module controls the pressure generator to inexsufflate the subject in accordance with the target parameter for machine-induced inexsufflation.

It is yet another aspect of one or more embodiments of the present invention to provide a method for synchronizing machine-induced inexsufflation with diaphragmatic pacing of a subject. The method comprises generating a pressurized flow of breathable gas for delivery to an airway of the subject; generating one or more output signals conveying information related to one or both of one or more gas parameters of a flow of breathable gas being breathed by the subject and/or one or more respiratory parameters of the subject; obtaining one or more configurable operational settings of diaphragmatic pacing of the subject; detecting an onset of a first inhalation of the subject, for a first respiratory cycle, the detection based on the one or more output signals, wherein the first inhalation is included in a first respiratory cycle; determining, responsive to detection of the onset of the first inhalation of the subject, a target parameter for machine-induced inexsufflation during a second respiratory cycle in synchrony with diaphragmatic pacing of the subject, wherein the second respiratory cycle is subsequent to the first respiratory cycle, and wherein the target parameter is an onset of inhalation during the second respiratory cycle or an onset of exhalation during the second respiratory cycle; and controlling a pressure generator to inexsufflate the subject in accordance with the determined target parameter for machine-induced inexsufflation during the second respiratory cycle.

It is yet another aspect of one or more embodiments to provide a system configured for synchronizing machine-induced inexsufflation with diaphragmatic pacing of a subject. The system comprises various means for different functions. The system includes pressure means for generating a pressurized flow of breathable gas for delivery to an airway of the subject. The system further includes means for generating one or more output signals conveying information related to one or both of one or more gas parameters of a flow of breathable gas being breathed by the subject and/or one or more respiratory parameters of the subject. The system further includes means for obtaining one or more configurable operational settings of diaphragmatic pacing of the subject. The system further includes means for detecting an onset of a first inhalation of the subject, for a first respiratory cycle, the detection based on the one or more output signals, wherein the first inhalation is included in a first respiratory cycle. The system further includes means for determining, responsive to operation of the means for detection the onset of the first inhalation of the subject, a target parameter for machine-induced inexsufflation during a second respiratory cycle in synchrony with diaphragmatic pacing of the subject, wherein the second respiratory cycle is subsequent to the first respiratory cycle, and wherein the target parameter is an onset of inhalation during the second respiratory cycle or an onset of exhalation during the second respiratory cycle. The system further includes means for controlling the pressure means to inexsufflate the subject in accordance with the determined target parameter for machine-induced inexsufflation during the second respiratory cycle.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF EXEMPLARY EMBODIMENTS

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

Figure 1:
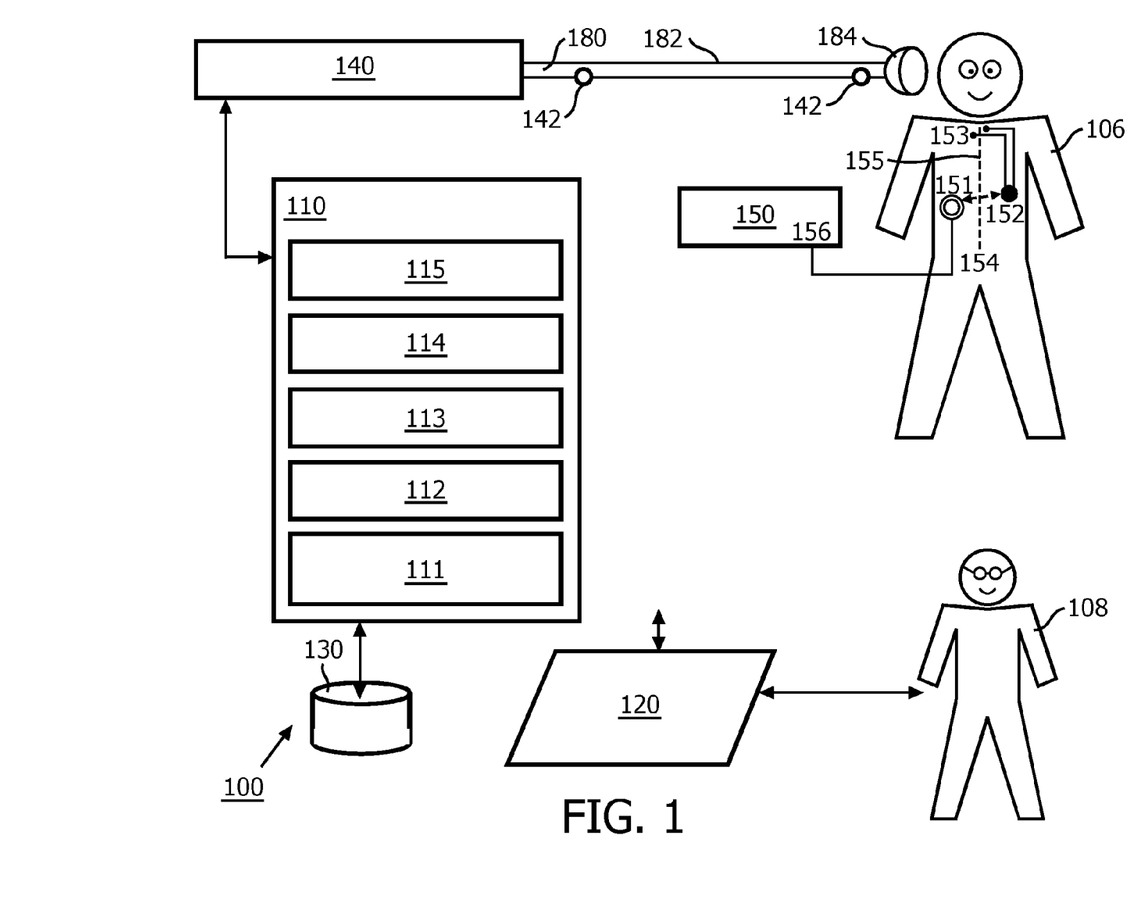
FIG. 1 schematically illustrates a system configured to synchronize inexsufflation and diaphragm pacing of a subject according to one or more embodiments.

FIG. 1 schematically illustrates an exemplary embodiment of a system 100 to synchronize machine-induced inexsufflation of a subject 106 and diaphragm pacing by a diaphragm pacer 150 of subject 106. Inexsufflation may loosen and/or expel secretions. Unaided inexsufflation may be difficult and/or impossible for a wide range of patients due to a wide range of medical conditions. The efficacy of an individual inexsufflation (e.g. during an individual respiratory cycle) may be quantified using one or more characteristic parameters, including (peak) flow rate, expelled (gas) volume, and/or other parameters.

Diaphragm pacer 150 may interchangeably be referred to as a diaphragm pacing device, a diaphragmatic pacer, a diaphragmatic pacing device, diaphragm pacemaker, breathing pacemaker, phrenic nerve pacer, phrenic nerve stimulator, and/or other terms or combination of terms. Diaphragm pacer 150 may rhythmically apply electrical impulses and/or stimulation to a diaphragm 154 of subject, to an area near diaphragm 154, to one or more nerves related to diaphragm 154 of subject 106 such as phrenic nerve 155, and/or to other areas or locations. Diaphragm pacer 150 may include a transmitter 156, an antenna 151, a receiver 152, one or more electrodes 153, and/or other components. Diaphragm pacer 150 may be configured to transmit electrical signals via transmitter 156 through antenna 151. These electrical signals may be received through receiver 152, which may be configured to be surgically implanted in subject 106.

Receiver 152 may be electrically coupled to one or more electrodes 153, which may be configured to be surgically implanted in subject 106 at or near phrenic nerve 155. Electric pulses through the one or more electrodes 153 may stimulate phrenic nerve 155. Responsive to the application of electrical impulses and/or stimulation, diaphragm 154 of subject 106 may contract, causing inspiration. Subsequently removing and/or reducing the stimulation may relax the diaphragm of the subject, causing expiration. By rhythmically pacing the diaphragm in this manner a breathing pattern may be established. Operational settings of diaphragmatic pacing may include one or more of a respiratory rate, inhalation period, exhalation period, one or more pause periods, inhalation-to-exhalation (period) ratio (this may be referred to as "I:E ratio"), an indicator of flow rate, an indicator of inspiratory volume, tidal volume, minute volume, and/or other operational setting that is related through a previously known and/or (calibrated) mathematical relationship to a respiratory parameter of subject 106. Operational settings may be expressed in different units, percentages, fractions, and/or other suitable expressions.

System 100 includes one or more of diaphragm pacer 150, a pressure generator 140, a user interface 120, a delivery circuit 180, electronic storage 130, one or more sensors 142, one or more processors 110, a configuration module 111, a detection module 112, a target module 113, a control module 114, a parameter determination module 115, and/or other components. System 100 may be dedicated to providing inexsufflations. Alternatively, and/or simultaneously, system 100 may provide other functions in addition to inexsufflation. In some embodiments, system 100 in FIG. 1 may be integrated, combined, or connected with a ventilator device or a diaphragm pacing device.

Pressure generator 140 is configured to provide a pressurized flow of breathable gas for delivery to and/or from the airway of subject 106, e.g. via delivery circuit 180. Delivery may use one or more pathways for fluidly communicating the breathable gas to and/or from the airway of subject 106. The direction and/or magnitude of the fluid communication may be selectively controlled, e.g. per individual pathway. Pressure generator 140 may be configured to adjust one or more of positive and/or negative pressure levels, flow rate, volume, humidity, velocity, acceleration, and/or other parameters of the pressurized flow of breathable gas.

Delivery circuit 180 is configured to selectively control the direction and/or flow of breathable gas to and/or from the airway of subject 106. Delivery circuit 180 may sometimes be referred to as subject interface 180. Delivery circuit 180 may be configured to operate in a first mode, a second mode, a third mode, and/or in other modes. In the first mode, delivery circuit 180 may be closed such that substantially no gas is communicated with the airway of subject 106 therethrough. In the second mode, delivery circuit 180 may be opened to permit gas to be exhausted from the airway of subject 106 through delivery circuit 180, e.g. to ambient atmosphere. In the third mode, delivery circuit 180 may be opened to permit gas to be delivered to the airway of subject 106 through delivery circuit 180, e.g. from pressure generator 140.

In various modes of operation of system 100, transitions between modes, and/or combinations of modes, system 100 may be used to provide respiratory functionality. For example, by way of non-limiting example, a breathing pattern or inexsufflation having particular respiratory and/or pneumatic characteristics. Respiratory cycles in the provided respiratory functionality may include inhalation periods, exhalation periods, pause periods therebetween, and/or other characteristics, which may correspond to the various modes of operation described herein. The provided respiratory functionality may be mechanical, machine-induced, machine-assisted, and/or any combination thereof.

In some implementations, delivery circuit 180 may include one or more of a valve and/or another pressure regulating device. In one embodiment delivery circuit 180 may include multiple valves in series and/or in parallel. Examples of suitable valves and/or other pressure regulating devices include a plug valve, a ball valve, a check valve, a butterfly valve, a solenoid, and/or other pressure regulating devices. Pressure regulating devices may be controlled hydraulically, pneumatically, via an electric motor and/or another mode of control configured to open and/or close a valve and/or other pressure control device.

Delivery circuit 180 may include a conduit 182 and/or a subject interface appliance 184. Conduit 182 may include a flexible length of hose, or other conduit, either in single-limb or dual-limb configuration that places subject interface appliance 184 in fluid communication with pressure generator 140. Conduit 182 forms a flow path through which a flow of breathable gas (e.g. air) may be communicated between subject interface appliance 184 and pressure generator 140.

Subject interface appliance 184 of system 100 in FIG. 1 is configured to deliver the pressurized flow of breathable gas to and/or from the airway of subject 106. As such, subject interface appliance 184 may include any appliance suitable for this function. In some embodiments, subject interface appliance 184 is configured to engage the airway of subject 106 without an intervening appliance. In this embodiment, subject interface appliance 184 may include one or more of an endotracheal tube, a nasal cannula, a tracheotomy tube, a nasal mask, a nasal/oral mask, a full-face mask, a total facemask, and/or other interface appliances that communicate a flow of gas with an airway of a subject. In some embodiments, pressure generator 140 is a dedicated ventilation device and subject interface appliance 184 is configured to be removably coupled with another interface appliance being used to deliver respiratory therapy to subject 106. For example, subject interface appliance 184 may be configured to engage with and/or be inserted into an endotracheal tube, a tracheotomy portal, and/or other interface appliances. The present disclosure is not limited to these examples, and contemplates fluid communication of breathable gas to and/or from subject 106 using any subject interface.

Electronic storage 130 of system 100 in FIG. 1 comprises electronic storage media that electronically stores information. The electronic storage media of electronic storage 130 may include one or both of system storage that is provided integrally (i.e., substantially non-removable) with system 100 and/or removable storage that is removably connectable to system 100 via, for example, a port (e.g., a USB port, a FireWire port, etc.), a slot (e.g., an SD card slot, etc.), or a drive (e.g., a disk drive, etc.). Electronic storage 130 may include one or more of optically readable storage media (e.g., optical disks, etc.), magnetically readable storage media (e.g., magnetic tape, magnetic hard drive, floppy drive, etc.), electrical charge-based storage media (e.g., EPROM, EEPROM, RAM, etc.), solid-state storage media (e.g., flash drive, etc.), and/or other electronically readable storage media. Electronic storage 130 may store software algorithms, information determined by processor 110, information received via user interface 120, and/or other information that enables system 100 to function properly. For example, electronic storage 130 may record or store information pertaining to individual inexsufflations and/or treatments that include one or more inexsufflations (as discussed elsewhere herein), and/or other information. Electronic storage 130 may be a separate component within system 100, or electronic storage 130 may be provided integrally with one or more other components of system 100 (e.g., processor 110).

User interface 120 of system 100 in FIG. 1 is configured to provide an interface between system 100 and a user (e.g., user 108, subject 106, a caregiver, a therapy decision-maker, etc.) through which the user can provide information to and receive information from system 100. This enables data, results, and/or instructions and any other communicable items, collectively referred to as "information," to be communicated between the user and system 100. An example of information that may be conveyed to user 108 is a report detailing information pertaining to individual inexsufflations throughout a period during which the subject is receiving treatment and/or therapy. Examples of information obtained from user 108 through user interface 120 may be one or more configurable operational settings (for system 100 and/or diaphragm pacer 150), such as a respiratory rate. Examples of interface devices suitable for inclusion in user interface 120 include a keypad, buttons, switches, a keyboard, knobs, levers, a display screen, a touch screen, speakers, a microphone, an indicator light, an audible alarm, and a printer. Information may be provided to user 108 or subject 106 by user interface 120 in the form of auditory signals, visual signals, tactile signals, and/or other sensory signals. In some embodiments, an electronic display may be integrated, embedded, and/or combined with user interface 120.

It is to be understood that other communication techniques, either hard-wired or wireless, are also contemplated herein as user interface 120. For example, in one embodiment, user interface 120 may be integrated with a removable storage interface provided by electronic storage 130. In this example, information is loaded into system 100 from removable storage (e.g., a smart card, a flash drive, a removable disk, etc.) that enables the user(s) to customize system 100. Other exemplary input devices and techniques adapted for use with system 100 as user interface 120 include, but are not limited to, an RS-232 port, RF link, an IR link, modem (telephone, cable, Ethernet, internet or other). In short, any technique for communicating information with system 100 is contemplated as user interface 120.

One or more sensors 142 of system 100 in FIG. 1 are configured to generate output signals conveying measurements related to gas parameters of respiratory airflow, airway mechanics, and/or respiratory parameters of subject 106. These parameters may include one or more of flow rate, (airway) pressure, humidity, velocity, acceleration, and/or other gas or respiratory parameters. Alternatively, and/or simultaneously, these parameters may pertain to one or more gas levels at or near the airway of subject 106, for example within subject interface appliance 184. As depicted in FIG. 1, one or more sensors 142 may be in fluid communication with conduit 182 and/or subject interface appliance 184. In some embodiments, one or more sensors 142 may generate output signals related to physiological parameters pertaining to subject 106, including, without limitation, the heart rate of subject 106. By way of non-limiting example, one or more sensors 142 may include a pressure band.

The illustration of sensor 142 including two members in FIG. 1 is not intended to be limiting. The illustration of a sensor 142 at or near subject interface appliance 184 is not intended to be limiting. The illustration of a sensor 142 at or near pressure generator 140 is not intended to be limiting. In one embodiment sensor 142 includes a plurality of sensors operating as described above by generating output signals conveying information related to parameters associated with the state and/or condition of an airway of subject 106, the breathing of subject 106, the gas breathed by subject 106, the composition of the gas breathed by subject 106, the delivery of the gas to the airway of subject 106, and/or a respiratory effort by the subject. For example, a parameter may be related to a mechanical unit of measurement of a component of pressure generator 140 (or of a device that pressure generator 140 is integrated, combined, or coupled with) such as valve drive current, rotor speed, motor speed, blower speed, fan speed, or a related measurement that may serve as a proxy for any of the previously listed parameters through a previously known and/or (calibrated) mathematical relationship. Resulting signals or information from the one or more sensors 142 may be transmitted to processor 110, user interface 120, electronic storage 130, and/or other components of system 100. This transmission may be wired and/or wireless.

Processor 110 of system 100 in FIG. 1 is configured to provide information processing capabilities in system 100. As such, processor 110 includes one or more of a digital processor, an analog processor, a digital circuit designed to process information, an analog circuit designed to process information, a state machine, and/or other mechanisms for electronically processing information. Although processor 110 is depicted in FIG. 1 as a single entity, this is for illustrative purposes only. In some embodiments, processor 110 may include a plurality of processing units.

As is shown in FIG. 1, processor 110 is configured to execute one or more computer program modules. The one or more computer program modules include one or more of configuration module 111, detection module 112, target module 113, control module 114, parameter determination module 115, and/or other modules. Processor 110 may be configured to execute modules 111-115 by software; hardware; firmware; some combination of software, hardware, and/or firmware; and/or other mechanisms for configuring processing capabilities on processor 110.

It should be appreciated that although modules 111-115 are illustrated in FIG. 1 as being co-located within a single processing unit, in embodiments in which processor 110 includes multiple processing units, one or more of modules 111-115 may be located remotely from the other modules. The description of the functionality provided by the different modules 111-115 described herein is for illustrative purposes, and is not intended to be limiting, as any of modules 111-115 may provide more or less functionality than is described. For example, one or more of modules 111-115 may be eliminated, and some or all of its functionality may be incorporated, shared, integrated into, and/or otherwise provided by other ones of modules 111-115. Note that processor 110 may be configured to execute one or more additional modules that may perform some or all of the functionality attributed below to one of modules 111-115.

Parameter determination module 115 of system 100 in FIG. 1 is configured to determine one or more gas parameters, respiratory parameters, and/or other parameters from output signals generated by sensor(s) 142. The one or more gas parameter may include and/or be related to one or more of (peak) flow, flow rate, (tidal) volume, pressure, temperature, humidity, velocity, acceleration, gas composition (e.g. concentration(s) of one or more constituents such as, e.g., $CO_2$), thermal energy dissipated, gas leak, and/or other measurements related to the flow of breathable gas. One or more respiratory parameters may be derived from gas parameters and/or other output signals conveying measurements of a flow of breathable gas delivered to and/or from the airway of subject 106. The one or more respiratory parameters may include one or more of respiratory rate, breathing period, inhalation time or period, exhalation time or period, inhalation-to-exhalation pause period, exhalation-to-inhalation pause period, respiration flow curve shape, transition time from inhalation to exhalation and/or vice versa, transition time from peak inhalation flow rate to peak exhalation flow rate and/or vice versa, respiration pressure curve shape, maximum proximal pressure drop (per breathing cycle and/or phase), peak cough flow, average (or otherwise aggregated) cough flow, inspiratory tidal volume (for one or more respiratory cycles), expiratory tidal volume (for one or more respiratory cycles), and/or other respiratory parameters. Respiratory parameters may be determined on a breath-by-breath basis, on a cough-by-cough basis, and/or at other intervals.

For example, a peak cough flow parameter may be determined for individual respiratory cycles and/or individual inexsufflations. The peak cough flow parameter may be used to determine how effectively subject 106 is able to clear secretions. For example, inspiratory tidal volume may be determined for individual respiratory cycles and/or individual inexsufflations. The inspiratory tidal volume may be used to determine how effectively subject 106 is able to clear secretions. Using other parameters described herein, and/or combinations thereof, in forming such a determination is contemplated within the scope of this disclosure.

Configuration module 111 of system 100 in FIG. 1 is configured to obtain configurable operational settings of diaphragmatic pacing of subject 106. In some embodiments, one or more configurable operational settings may be obtained, e.g. manually, from a user and/or subject 106, e.g. through user interface 120. In such a manual mode, subject 106 may conjunctionally set and/or program diaphragm pacer 150 and system 100 such that both use the same respiratory rate (or breathing frequency), and/or the same or similar other respiratory parameters.

In some embodiments, one or more configurable operational settings may be obtained through electric and/or electronic signal transfer from diaphragm pacer 150 to system 100. Diaphragm pacer 150 may be configured to perform the diaphragmatic pacing of subject 106 described herein. In such a data-link mode, the electronic transfer may be intentional or unintentional (from the viewpoint of diaphragm pacer 150 and/or the intended or envisioned functionality thereof). In some embodiments, intentional signal transfer may be used by diaphragm pacer 150 that is configured to broadcast and/or transmit information pertaining to one or more configurable operational settings, for example through one or more of transmitter 156, antenna 151, and/or other components of diaphragm pacer 150. Alternatively, and/or simultaneously, unintentional signal transfer may be used when a signal between, e.g., diaphragm pacer 150 and diaphragm 154 of subject 106 is intercepted by system 100 such that information pertaining to one or more configurable operation settings may be extracted from the intercepted signal. For example, one or more sensors 142 may be configured to generate output signals conveying information related to information transmitted by diaphragm pacer 150 in a manner similar to receiver 152 of diaphragm pacer 150.

Figure 2:
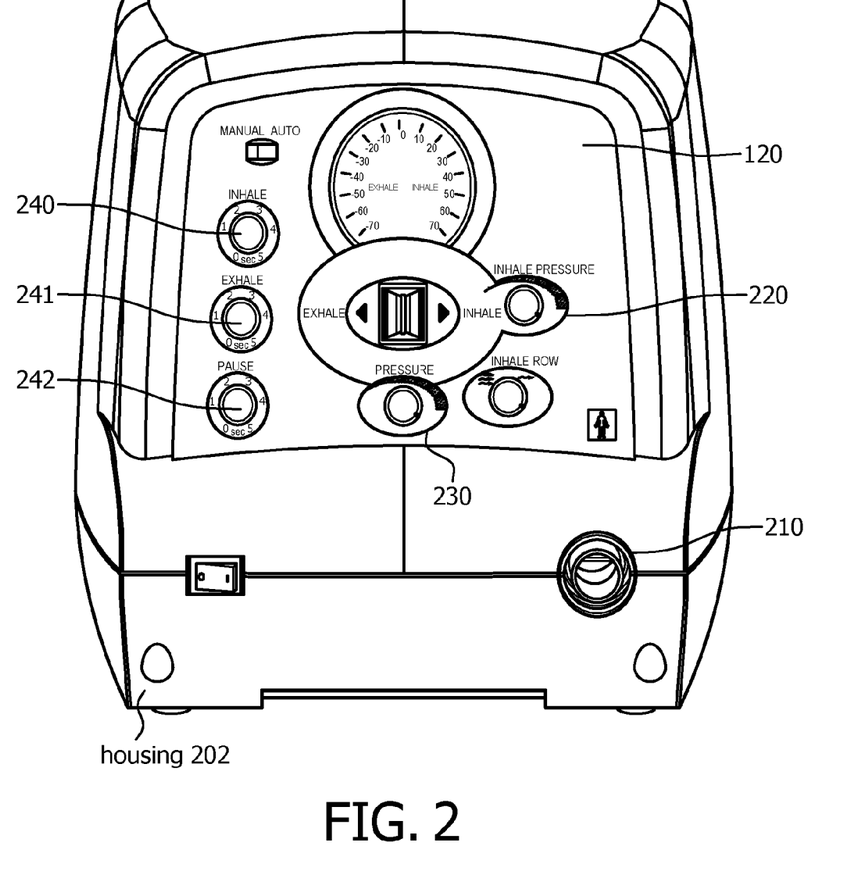
FIG. 2 illustrates a system configured to synchronize inexsufflation and diaphragm pacing of a subject according to one or more embodiments.

By way of illustration, FIG. 2 illustrates one embodiment of system 100 in which some of the components are housed in a housing 202. A port 210 is formed in housing 202. The port 210 is configured to communicate a (pressurized) flow of breathable gas with system 100. In the embodiment shown in FIG. 2, user interface 120 may be carried on or by housing 202. User interface 120 is shown as including inhale pressure knob 220 and (exhale) pressure knob 230, which may be used to set a first pressure level and a second pressure level for the inexsufflation, inhalation period knob 240, exhalation period knob 241, pause period knob 242, which are used to set the respective periods from 0 to about 5 seconds. The pause period in this embodiment may be inserted between an exhalation and the subsequent inhalation. The embodiment depicted in FIG. 2 is intended to be exemplary, and is not meant to be limiting in any way.

Referring to FIG. 1, in some embodiments, one or more configurable operational settings may be obtained through one or more generated output signals from the one or more sensors 142. For example, the respiratory rate of subject 106 may be determined based on the output signals from a pressure band and/or a flow rate sensor.

Detection module 112 of system 100 in FIG. 1 is configured to detect onsets of inhalations and/or exhalations of subjects during respiratory cycles. Detection module 112 may be configured to detect the onset of a first inhalation during a first respiratory cycle. Detection module 112 may be configured to detect the onset of a first exhalation during a first respiratory cycle. Detections by detection module 112 may be based on one or more output signals generated by one or more sensors 142. Responsive to detection of onsets of inhalations and exhalations the detected timing information may be used to determine one or more of respiratory rate, phase of the breathing pattern, inhalation period, exhalation period, pause period, and/or other respiratory parameters. Derivatives thereof, such as I:E ratio, may also be determined.

Target module 113 is configured to determine one or more target parameters for machine-induced inexsufflation during one or more (subsequent) respiratory cycles such that, responsive to detections by detection module 112, target module 113 determines one or more target parameters for machine-induced inexsufflation performed in synchrony with diaphragmatic pacing of subject 106. An inexsufflation may include an insufflation and an exsufflation. Efficacy and/or comfort may be improved by aligning and/or synchronizing machine-induced insufflation with the inhalation of the breathing pattern of the subject, and/or by aligning and/or synchronizing machine-induced exsufflation with the exhalation of the breathing pattern of the subject. For proper synchronization it may not be sufficient to match merely the breathing rate. The target parameters may correspond to one or more of the onset and/or phase of inhalation and/or exhalation. For example, efficacy and/or comfort of respiratory therapy may be improved when the onset of inhalation (during diaphragmatic pacing) corresponds to the onset of machine-induced insufflation, and/or the onset of exhalation corresponds to the onset of machine-induced exsufflation. Target parameters for machine-induced inexsufflation may include one or more pressure levels, amplitudes, slopes, rates, and/or any other configurable operational condition or parameter that may be used for machine-induced inexsufflation.

Control module 114 of system 100 in FIG. 1 is configured to control operation of system 100 during inexsufflation of subject 106. Control module 111 may be configured to control pressure generator 140 to adjust one or more levels of one or more gas parameters of the pressurized flow of breathable gas in accordance with one or more of a (respiratory) therapy regimen, one or more algorithms that control adjustments and/or changes in the pressurized flow of breathable gas, and/or other factors. Control module 114 may be configured to control pressure generator 140 such that one or more gas parameters of the pressurized flow of breathable gas are varied over time in accordance with a respiratory therapy regimen and/or treatment. Control module 114 may be configured to control pressure generator 140 to provide the pressurized flow of breathable gas at inhalation pressure levels during inhalation phases, and/or at exhalation pressure levels during exhalation phases.

For example, pressure of the pressurized flow of breathable gas may be elevated (e.g., with regard to ambient atmosphere) during inhalation to insufflate subject 106. During this insufflation, one or more of a flow rate, an insufflation pressure, and/or an inhaled volume may be controlled by control module 114. Responsive to the insufflation being completed (e.g., as determined in accordance with the therapy regimen), control module 114 may be configured to cause pressure generator 140 to reduce pressure of the pressurized flow of breathable gas (e.g., to below ambient atmosphere and/or to a negative pressure, or some other pressure lower than the insufflation pressure) to cause the gas in the lungs and/or airway of subject 106 to be expelled and/or drawn out quickly, thereby exsufflating subject 106.

Parameters determined by parameter determination module 115 and/or received through one or more sensors 142 may be used by control module 114, e.g. in a feedback manner, to adjust therapy modes/settings/operations of system 100. Alternatively, and/or simultaneously, signals and/or information received through user interface 120 may be used by control module 114, e.g. in a feedback manner, to adjust one or more therapy modes/settings/operations of system 100. In some embodiments, user 108 may (e.g. manually) control one or more pressure levels used during operation of system 100 through user interface 120. Control module 114 may be configured to time its operations relative to the transitional moments in the breathing cycle of a subject, over multiple breath cycles, and/or in any other relation to any detected events and/or occurrences.

In some embodiments, operation of one or more modules, including control module 114, may be governed through programmatic control, e.g. by an algorithm implemented through instructions that are executed by a module. Such an algorithm may be designed to titrate operating conditions of system 100 such that a target operating condition is reached and/or accomplished over time. Through the algorithm, one or more gas parameters of the pressurized flow of breathable gas may be adjusted, such as for example the inspiratory pressure level, based on a determined parameter of one or more recent respiratory cycles or inexsufflations. In some embodiments, alternatively and/or simultaneously, the algorithm may be designed to reach a target inspiratory tidal volume for individual inexsufflations.

It will be appreciated that the description of the operation of pressure generator 140 by the electronic processor 110 and/or its modules is not intended to be limiting. Other controllers for opening pressure generator 140 responsive to pressurization along delivery circuit 180 fall within the scope of this disclosure. Other mechanical controllers are also contemplated.

Figure 3:
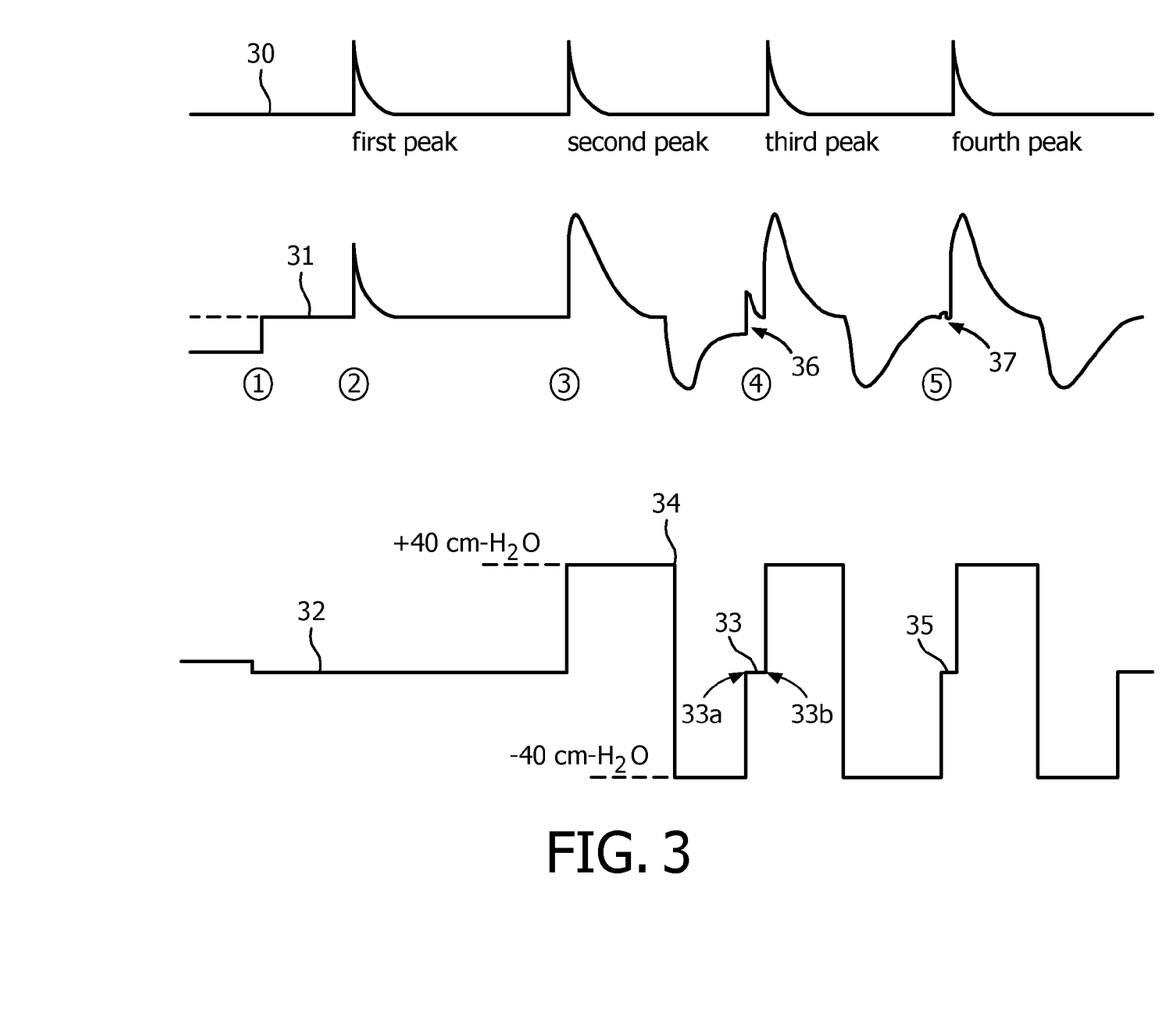
FIG. 3 illustrates plots of pressure and flow during inexsufflation.

By way of illustration, FIG. 3 shows plots of flow and pressure at or near the airway of a subject undergoing diaphragmatic pacing and/or synchronized inexsufflation over time. Graph 30 illustrates respiratory effort through diaphragmatic pacing in terms of patient flow as it changes over time. Graph 30 spans about four respiratory cycles of the subject. The depiction of four occurrences of temporary peaks of patient flow in graph 30 as labeled is merely exemplary, and not intended to be limiting in any way. These peaks may be referred to as first peak, second peak, and so on. Graph 31 illustrates measured patient flow as it changes over time. The reference numbers 1 through 5, each depicted inside a circle along graph 31 in FIG. 3, correspond to five moments or events as described below. Graph 32 illustrates a level of pressure of a pressurized flow of breathable gas over time as provided by a pressure generator. The level of pressure ranges between plus and minus 40 cm-H$_2$O in this example. The level of pressure depicted in graph 32 may be based on the measured patient flow of graph 31. Note that graphs 30-31-32 may share a similar horizontal time axis, such that moments and/or events may correspond between these graphs.

At moment "1", a pressure generator is activated such that a small positive pressure is provided to the subject. At moment "2", an onset of a first inhalation is detected, which may correspond to the first peak in graph 30. At moment "3", an onset of a second inhalation subsequent to the first inhalation is detected, which may correspond to the second peak in graph 30. Based on the relative timing of moment "2" and moment "3" a current breathing rate of the subject may be determined. Note that the current breathing rate may (typically gradually) change over the course of multiple respiratory cycles. Responsive to moment "3" in graph 31, the pressure generator may provide a level of positive pressure to aid the first insufflation of the subject, as depicted in graph 32 by the elevation of the pressure level to +40 cm-H$_2$O. An event labeled 34 may indicate the end of the first insufflation and/or the onset of the first exsufflation in graph 32, as depicted by the reduction of the pressure level to −40 cm-H$_2$O. The inhalation period of the respiratory cycle corresponding to moment "3" may span from moment "3" to the timing of event 34. Pause period 33 may indicate a pause period between exsufflation and subsequent insufflation. Pause period 33 may span from onset 33a of the pause period to end 33b of the pause period. At or near moment "4", the first machine-induced inexsufflation performed in synchrony with diaphragmatic pacing of the subject is complete and an onset of a third inhalation subsequent to the second inhalation is detected, which may correspond to the third peak in graph 30.

Breath staking near moment "4" in graph 31 (in other words, flow perturbation 36 in graph 31 immediately before a peak corresponding to the third peak in graph 30) may be caused by using an I:E ratio for the first machine-induced inexsufflation that differs from the I;E ratio of the breathing pattern of the subject. Based on generated output signals and/or detections of transitional moments within the breathing pattern (as described elsewhere herein), operational parameters for the inexsufflation, including for example the I:E ratio, may be adjusted from breath to breath or over the course of multiple respiratory cycles. For example, at or near moment "5", the second machine-induced inexsufflation performed in synchrony with diaphragmatic pacing of the subject is complete and an onset of a fourth inhalation subsequent to the third inhalation is detected, which may correspond to the fourth peak in graph 30. By virtue of the adjustments described herein, breath staking in graph 32 at flow perturbation 37 may be reduced in comparison to breath staking at flow perturbation 36. Pause period 35 may indicate a pause period between exsufflation and subsequent insufflation. Pause period 35 may be different, e.g. shorter as indicated in this example, than a previous pause period, such as pause period 33. Such a change may contribute to a gradually smoother pressure level over the span of multiple respiratory cycles, as depicted in graph 31. Alternatively, and/or simultaneously, the inhalation period, exhalation period, and/or I:E ratio as depicted by graph 32 may be adjusted between subsequent inexsufflations or respiratory cycles of the subject in pursuit of improved efficacy (of the inexsufflations) and/or comfort for the subject.

Figure 4:
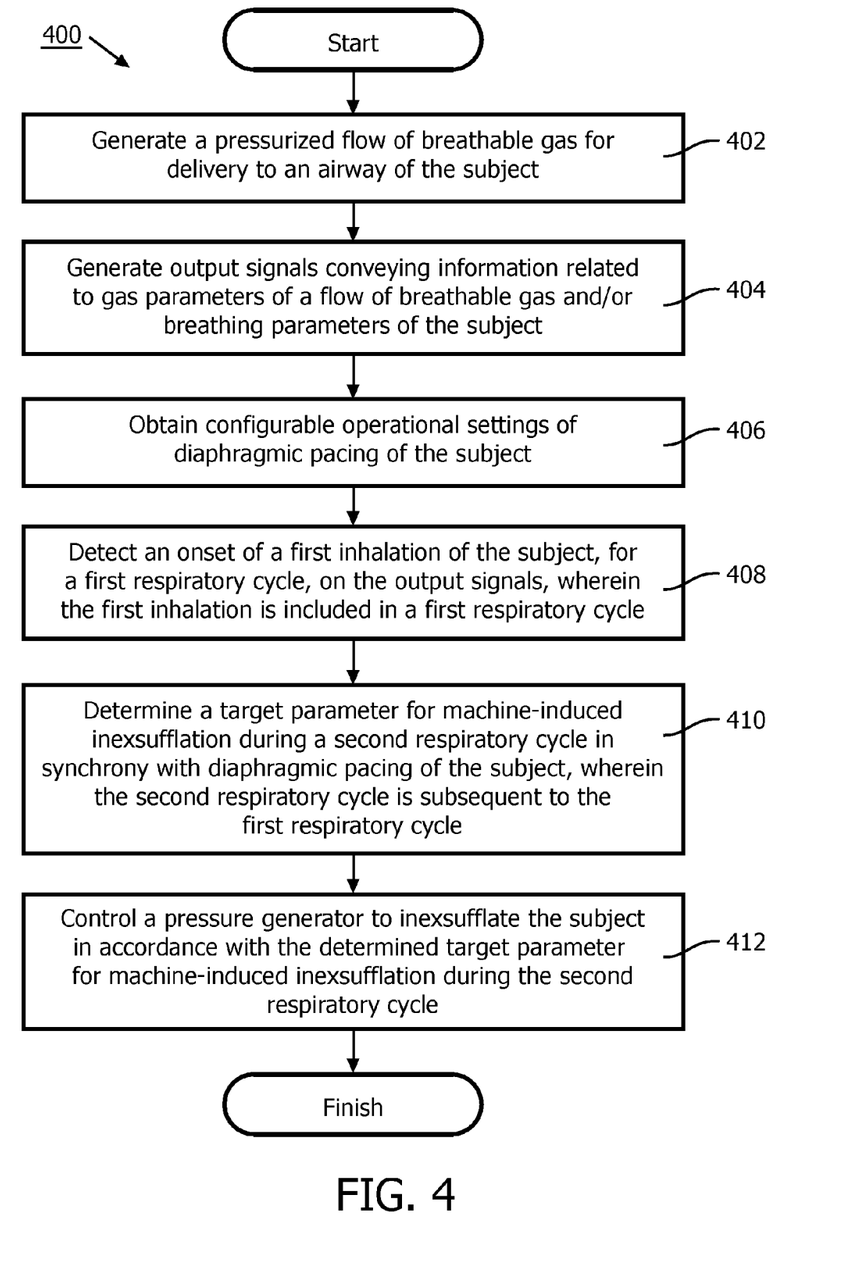
FIG. 4 illustrates a method configured to synchronize inexsufflation and diaphragm pacing of a subject according to one or more embodiments.

FIG. 4 illustrates a method 400 of synchronizing inexsufflation and diaphragmatic pacing of a subject. The operations of method 400 presented below are intended to be illustrative. In some embodiments, method 400 may be accomplished with one or more additional operations not described, and/or without one or more of the operations discussed. Additionally, the order in which the operations of method 400 are illustrated in FIG. 4 and described below is not intended to be limiting.

In some embodiments, method 400 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 400 in response to instructions stored electronically on an electronic storage medium. The one or more processing devices may include one or more devices configured through hardware, firmware, and/or software to be specifically designed for execution of one or more of the operations of method 400.

At an operation 402, a pressurized flow of breathable gas is generated for delivery to an airway of the subject. In some embodiments, operation 402 is performed by a pressure generator similar to or substantially the same as pressure generator 140 (shown in FIG. 1 and described herein).

At an operation 404, one or more output signals are generated conveying information related to one or both of one or more gas parameters of a flow of breathable gas being breathed by the subject and/or one or more respiratory parameters of the subject. In some embodiments, operation 404 is performed by a sensor similar to or substantially the same as one or more sensors 142 (shown in FIG. 1 and described herein).

At an operation 406, one or more configurable operational settings of diaphragmatic pacing of the subject are obtained. In some embodiments, operation 406 is performed through a user interfaced similar to or substantially the same as user interface 120 (shown in FIG. 1 and described herein).

At an operation 408, an onset of a first inhalation of the subject is detected, for a first respiratory cycle, the detection based on the one or more output signals. The first inhalation is included in a first respiratory cycle. In some embodiments, operation 408 is performed by a detection module similar to or substantially the same as detection module 112 (shown in FIG. 1 and described herein).

At an operation 410, responsive to detection of the onset of the first inhalation of the subject, a target parameter for machine-induced inexsufflation is determined during a second respiratory cycle in synchrony with diaphragmatic pacing of the subject. The second respiratory cycle is subsequent to the first respiratory cycle. The target parameter is an onset of inhalation during the second respiratory cycle or an onset of exhalation during the second respiratory cycle. In some embodiments, operation 410 is performed by a target module similar to or substantially the same as target module 113 (shown in FIG. 1 and described herein).

At an operation 412, a pressure generator is controlled to inexsufflate the subject in accordance with the determined target parameter for machine-induced inexsufflation during the second respiratory cycle. In some embodiments, operation 412 is performed by a control module similar to or substantially the same as control module 114 (shown in FIG. 1 and described herein).

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A system for synchronizing machine-induced inexsufflation with a diaphragmatic pacing of a subject, the system comprising;
   a pressure generator configured to generate a pressurized flow of breathable gas for delivery to an airway of the subject;
   one or more sensors configured to generate one or more output signals conveying information related to one or both of
     i) one or more gas parameters of a flow of breathable gas being breathed by the subject and/or
     ii) one or more respiratory parameters of the subject; and
   one or more processors configured to execute computer program modules, the computer program modules comprising:
     a configuration module configured to obtain one or more configurable operational settings of the diaphragmatic pacing of the subject;
     a detection module configured to detect onsets of inhalations of the subject such that, for a first respiratory cycle, the detection module detects an onset of a first inhalation of the subject based on the one or more output signals, wherein the first inhalation is included in the first respiratory cycle;
     a target module configured to determine a target parameter for machine-induced inexsufflation during respiratory cycles such that, responsive to detection of the onset of the first inhalation, the target module determines the target parameter for machine-induced inexsufflation during a second respiratory cycle such that the machine-induced inexsufflation occurs in synchrony with the diaphragmatic pacing of the subject, wherein the second respiratory cycle is subsequent to the first respiratory cycle, and wherein the target parameter corresponds to an onset of inhalation during the second respiratory cycle or an onset of exhalation during the second respiratory cycle; and
     a control module configured to control the pressure generator to inexsufflate the subject such that during the second respiratory cycle the control module controls the pressure generator to inexsufflate the subject in accordance with the target parameter for machine-induced inexsufflation, wherein:
       inexsufflating the subject comprises controlling the pressure generator to generate a pressure cycle providing a positive pressure during a first time period, a negative pressure during a second time period, and a pause in pressure generation during a third time period, wherein the third time period occurs subsequent to the second time period and the second time period occurs subsequent to the first time period; and
       at least two of the first, second, or third time periods are adjusted based on the target parameter in one or more subsequent pressure cycles to enhance synchronization of the machine-induced inexsufflation with the diaphragmatic pacing over multiple pressure or respiratory cycles.

2. The system of claim 1, further comprising a user interface configured to provide an interface between the system and a user through which the user can provide information to the system, wherein the configuration module is configured to obtain one or more configurable operational settings through the user interface.

3. The system of claim 1, wherein the configuration module is configured to obtain one or more operational settings through electronic signal transfer from a diaphragm pacing device configured to perform the diaphragmatic pacing of the subject.

4. The system of claim 1, wherein the one or more sensors include a pressure band configured to generate one or more output signals conveying information related to one or more respiratory parameters of the subject, wherein the detection module detects the onset of the first inhalation based on the one or more output signals generated by the pressure band, and wherein the configuration module is configured to obtain the one or more configurable operational settings based on the output signals generated by the pressure band.

5. The system of claim 1, wherein the one or more output signals convey information related to one or more gas parameters of the flow of breathable gas being breathed by the subject during one or more respiratory cycles, and wherein the configuration module is configured to obtain the one or more configurable operational settings based on the one or more output signals.

6. A method for synchronizing machine-induced inexsufflation with diaphragmatic pacing of a subject, the method comprising;
    generating one or more output signals conveying information related to one or both of
        i) one or more gas parameters of a flow of breathable gas being breathed by the subject and/or one,
        ii) or more respiratory parameters of the subject;
    obtaining one or more configurable operational settings of diaphragmatic pacing of the subject;
    detecting an onset of a first inhalation of the subject, for a first respiratory cycle, the detection based on the one or more output signals, wherein the first inhalation is included in a first respiratory cycle; and
    determining, responsive to detection of the onset of the first inhalation of the subject, a target parameter for machine-induced inexsufflation during a second respiratory cycle such that the machine-induced inexsufflation occurs in synchrony with diaphragmatic pacing of the subject, wherein:
        the second respiratory cycle is subsequent to the first respiratory cycle,
        the target parameter corresponds to an onset of inhalation during the second respiratory cycle or an onset of exhalation during the second respiratory cycle,
        inexsufflating the subject comprises controlling the pressure generator to generate a pressure cycle providing a positive pressure during a first time period, a negative pressure during a second time period, and a pause in pressure generation during a third time period,
        the third time period occurs subsequent to the second time period and the second time period occurs subsequent to the first time period, and
        at least of the first, second, or third time periods are adjusted based on the target parameter in one or more subsequent pressure cycles to enhance synchronization of the machine-induced inexsufflation with the diaphragmatic pacing over multiple pressure or respiratory cycles.

7. The method of claim 6, further comprising obtaining information from the user through a user interface, wherein one or more configurable operational settings are obtained from the user through the user interface.

8. The method of claim 6, wherein the one or more configurable operational settings are obtained through electronic signal transfer from a diaphragm pacing device configured to perform the diaphragmatic pacing of the subject.

9. The method of claim 6, wherein the one or more output signals that convey information related to one or more respiratory parameters of the subject are generated by a pressure band, wherein detecting the onset of the first inhalation is based on the one or more output signals generated by the pressure band, and wherein determining the target parameter is based on the one or more output signals generated by the pressure band.

10. The method of claim 6, wherein the one or more output signals convey information related to one or more gas parameters of the flow of breathable gas being breathed by the subject, wherein obtaining the one or more configurable operational settings is based on the one or more output signals.

11. A system configured for synchronizing machine-induced inexsufflation with a diaphragmatic pacing of a subject, the system comprising;
    pressure means for generating a pressurized flow of breathable gas for delivery to an airway of the subject;
    means for generating one or more output signals conveying information related to one or both of
        i) one or more gas parameters of a flow of breathable gas being breathed by the subject and/or
        ii) one or more respiratory parameters of the subject;
    means for obtaining one or more configurable operational settings of the diaphragmatic pacing of the subject;
    means for detecting an onset of a first inhalation of the subject, for a first respiratory cycle, the detection based on the one or more output signals, wherein the first inhalation is included in a first respiratory cycle;
    means for determining, responsive to operation of the means for detection the onset of the first inhalation of the subject, a target parameter for machine-induced inexsufflation during a second respiratory cycle such that the machine-induced inexsufflation occurs in synchrony with the diaphragmatic pacing of the subject, wherein the second respiratory cycle is subsequent to the first respiratory cycle, and wherein the target parameter corresponds to an onset of inhalation during the second respiratory cycle or an onset of exhalation during the second respiratory cycle; and
    means for controlling the pressure means to inexsufflate the subject in accordance with the determined target parameter for machine-induced inexsufflation during the second respiratory cycle, wherein:
        controlling the pressure means to inexsufflate the subject comprises controlling the pressure means to generate a pressure cycle providing a positive pressure during a first time period, a negative pressure during a second time period, and a pause in pressure generation during a third time period, the third time period occurs subsequent to the second time period and the second time period occurs subsequent to the first time period, and
        at least two of the first, second, or third time periods are adjusted based on the target parameter in one or more subsequent pressure cycles to enhance synchronization of the machine-induced inexsufflation with the diaphragmatic pacing over multiple pressure or respiratory cycles.

12. The system of claim 11, further comprising means for obtaining information from the user, wherein operation of the means for obtaining the one or more configurable operational settings is performed through the means for obtaining information from the user.

13. The system of claim 11, wherein operation of the means for obtaining the one or more configurable operational settings is performed through electronic signal transfer from a diaphragm pacing device configured to perform the diaphragmatic pacing of the subject.

14. The system of claim 11, wherein operation of the means for generating the one or more output signals that convey information related to one or more respiratory parameters of the subject is performed through a pressure band, wherein operation of the means for detecting the onset of the first inhalation is based on the one or more output signals generated by the pressure band, and wherein operation of the means for determining the target parameter is based on the one or more output signals generated by the pressure band.

15. The system of claim 11, wherein operation of the means for generating the one or more output signals conveys information related to one or more respiratory parameters of the subject, and wherein operation of the means for obtaining the one or more configurable operational settings is based on the one or more output signals.

16. The system of claim 1, wherein the one or more configurable operational settings of the diaphragmatic pacing of the subject include an inhalation to exhalation period (I:E) ratio, and wherein the I:E ratio is also adjusted based on the target parameter in one or more subsequent pressure cycles to enhance synchronization of the machine-induced inexsufflation with the diaphragmatic pacing over multiple pressure or respiratory cycles.

17. The method of claim 6, wherein the one or more configurable operational settings of the diaphragmatic pacing of the subject include an inhalation to exhalation period (I:E) ratio, and wherein the I:E ratio is also adjusted based on the target parameter in one or more subsequent pressure cycles to enhance synchronization of the machine-induced inexsufflation with the diaphragmatic pacing over multiple pressure or respiratory cycles.

18. The system of claim 11, wherein the one or more configurable operational settings of the diaphragmatic pacing of the subject include an inhalation to exhalation period (I:E) ratio, and wherein the I:E ratio is also adjusted based on the target parameter in one or more subsequent pressure cycles to enhance synchronization of the machine-induced inexsufflation with the diaphragmatic pacing over multiple pressure or respiratory cycles.

* * * * *